United States Patent [19]

Hoffmann et al.

[11] 4,229,444
[45] Oct. 21, 1980

[54] PESTICIDAL O-ALKYL-O-(1,5-DISUBSTITUTED-1,2,4-TRIAZOLYL-(3)-THIONO-PHOSPHORIC (PHOSPHONIC) ACID ESTERS AND ESTER-AMIDES

[75] Inventors: Hellmut Hoffmann, Wuppertal; Ingeborg Hammann, Cologne; Wolfgang Behrenz, Overath-Steinenbrück; Bernhard Homeyer, Opladen; Wilhelm Stendel, Wuppertal, all of Fed. Rep. of Germany

[73] Assignee: Bayer Aktiengesellschaft, Leverkusen, Fed. Rep. of Germany

[21] Appl. No.: 907,388

[22] Filed: May 18, 1978

Related U.S. Application Data

[60] Continuation of Ser. No. 645,971, Jan. 2, 1976, abandoned, which is a division of Ser. No. 430,435, Jan. 3, 1974, abandoned.

[30] Foreign Application Priority Data

Jan. 12, 1973 [DE] Fed. Rep. of Germany ....... 2301400

[51] Int. Cl.$^2$ ............................ A01N 9/36; C07F 9/65
[52] U.S. Cl. .................................. 424/200; 548/118; 548/264
[58] Field of Search .................. 260/308 R; 424/200; 548/118

[56] References Cited

U.S. PATENT DOCUMENTS

| | | | |
|---|---|---|---|
| 3,809,701 | 5/1974 | Dawes et al. | 260/308 R |
| 3,867,396 | 2/1975 | Bohner et al. | 260/308 R |
| 3,867,398 | 2/1975 | Bohner et al. | 260/308 R |
| 3,981,994 | 9/1976 | Hoffmann et al. | 260/308 R |
| 3,987,168 | 10/1976 | Hoffmann et al. | 260/308 R |
| 4,044,124 | 8/1977 | Boehner et al. | 260/308 R |
| 4,054,575 | 10/1977 | Böhner et al. | 260/308 R |
| 4,055,571 | 10/1977 | Hoffmann et al. | 424/200 |

*Primary Examiner*—Alton D. Rollins
*Attorney, Agent, or Firm*—Sprung, Felfe, Horn, Lynch & Kramer

[57] ABSTRACT

O-alkyl-O-[1,5-disubstituted-1,2,4-triazolyl-(3)]-thionophosphoric (phosphonic) acid esters and ester-amides of the formula $$\begin{array}{c} RO \\ \diagdown \\ R' \end{array} \!\!\! \begin{array}{c} S \\ \| \\ P-O- \end{array} \!\!\! \begin{array}{c} N= \\ \diagup \\ \diagdown \\ N-N \\ | \\ R''' \end{array} \!\!\! XR'' \qquad (I)$$

in which
R is alkyl of 1 to 6 carbon atoms,
R' is alkyl, alkoxy or alkylamino of 1 to 6 carbon atoms or phenyl,
R'' is alkyl or cyanoalkyl of 1 to 4 carbon atoms or alkenyl of 3 or 4 carbon atoms,
R''' is alkyl or cyanoalkyl with 1 to 6 carbon atoms in the alkyl radical, and
X is oxygen or sulfur,
which possess insecticidal and acaricidal properties.

5 Claims, No Drawings

PESTICIDAL O-ALKYL-O-(1,5-DISUBSTITUTED-1,2,4-TRIAZOLYL-(3)-THIONO-PHOSPHORIC (PHOSPHONIC) ACID ESTERS AND ESTER-AMIDES

This is a continuation of application Ser. No. 645,971, filed Jan. 2, 1976, now abandoned, which is a division of application Ser. No. 430,435, filed Jan. 3, 1974, now abandoned.

The present invention relates to and has for its objects the provision of particular new O-alkyl-O-[1,5-disubstituted-1,2,4-triazolyl-(3)]-thiono-phosphoric(phosphonic) acid esters and ester-amides which possess insecticidal or acaricidal properties, active compositions in the form of mixtures of such compounds with solid and liquid dispersible carrier vehicles, and methods for producing such compounds and for using such compounds in a new way especially for combating pests, e.g. insects and acarids, with other and further objects becoming apparent from a study of the within specification and accompanying examples.

It is known from U.S. Pat. No. 2,754,244 that pyrazolothionophosphoric acid esters, for example, O,O-dimethyl-(Compound A) and O,O-diethyl-O-[3-methyl-pyrazol(5)yl]-thionophosphoric acid esters (Compound B), possess insecticidal and acaricidal properties.

The present invention provides O-triazolylthionophosphoric(phosphonic) acid esters and ester-amides of the general formula

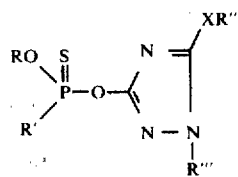

in which
R is alkyl of 1 to 6 carbon atoms,
R' is alkyl, alkoxy or alkylamino of 1 to 6 carbon atoms or phenyl,
R" is alkyl or cyanoalkyl of 1 to 4 carbon atoms or alkenyl of 3 or 4 carbon atoms,
R''' is alkyl or cyanoalkyl with 1 to 6 carbon atoms in the alkyl radical, and
X is oxygen or sulfur.

Preferably, R is lower alkyl of 1 to 4 carbon atoms, R' is lower alkyl or alkylamino of 1 to 4 carbon atoms or phenyl, R" is lower alkyl of 1 to 3 carbon atoms, alkenyl of 3 carbon atoms or cyanomethyl, and R''' is lower alkyl of 1 to 3 carbon atoms.

The alkyl groups may of course be branched or straight-chain.

Surprisingly, the O-triazolylthionophosphoric(phosphonic) acid esters and ester-amides according to the invention display a better insecticidal, especially soil-insecticidal, and acaricidal action than the previously known compounds of analogous structure and of the same type of action. The new products can not only be employed against insects which damage plants but also against hygiene pests and pests of stored products and/or in the veterinary medicine field against animal ectoparasites, for example parasitic fly larvae and ticks. They thus represent a genuine enrichment of the art. Furthermore, the new compounds contribute to reducing the constant demand for new preparations in the field of combating pests. This demand arises from the fact that the commercially available agents have to meet higher and higher standards, especially in respect of the protection of the environment, such as low toxicity to warm-blooded animals and phytotoxicity, rapid degradation in and on the plant with short periods which have to elapse between application of the pesticide and harvesting, and activity against resistant pests.

The invention also provides a process for the production of an O-triazolylthionophosphoric(phosphonic) acid ester or ester-amide of the formula (I) in which a thionophosphoric(phosphonic) acid ester-halide or ester-amide-halide of the general formula

in which
R and R' have the abovementioned meanings, and
Hal denotes halogen, preferably chlorine, is reacted with a triazolyl derivative of the general formula

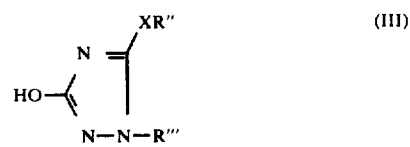

in which
X, R" and R''' have the abovementioned meanings, in the presence of an acid acceptor or in the form of an alkali metal salt, alkaline earth metal salt or ammonium salt.

If, for example, O,O-diethylthionophosphoric acid diester-chloride and 1-methyl-3-hydroxy-5-ethoxy-triazole-(1,2,4) are used as starting materials, the course of the reaction can be represented by the following formula scheme:

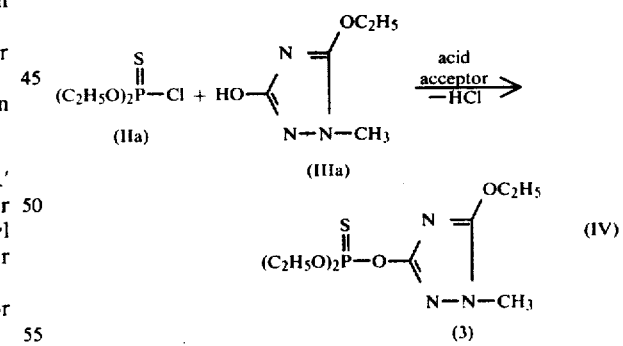

The formulae (II) and (III) provide an unambiguous general definition of the starting compounds to be used.

The thionophosphoric(phosphonic) acid derivatives (II) are known from the literature and can be prepared according to customary processes. As examples thereof, the following may be mentioned individually: O,O-dimethyl-, O,O-diethyl-, O,O-di-n-propyl, O,O-di-iso-propyl-, O,O-di-n-butyl, O,O-di-tert.-butyl, O-ethyl-O-n-propyl, O-ethyl-O-isopropyl- and O-ethyl-O-n-butyl-thionophosphoric acid ester-chloride, and also O-methyl-, O-ethyl-, O-n-propyl-, O-iso-propyl-, O-n-butyl-, O-iso-butyl, O-sec.-butyl- and O-tert.-butylmethane- or -ethane-, -propane- or -phenyl-thionophosphonic acid ester-chloride, as well as O-methyl-N-methyl, O-ethyl-N-methyl-, O-n-propyl-N-methyl-, O-iso-propyl-N-methyl-, O-n-butyl-N-methyl-, O-methyl-N-ethyl-, O-ethyl-N-n-propyl-, O-ethyl-N-iso-propyl-, O-n-propyl-N-ethyl-, O-iso-propyl-N-ethyl- and O-n-propyl-N-ethyl-thionophosphoric acid esteramide-chloride.

The triazoles of the formula (III), some of which are new, can be prepared by processes which are known in principle, in particular:

(a) If X represents sulfur, the known thiosemicarbazide derivatives of the general formula

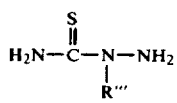
(V)

may be reacted, for example, with pyrocarbonic acid diethyl ester, to give intermediate products of the following general formula

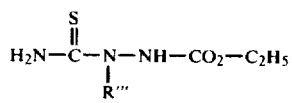
(VI)

in which

R''' has the abovementioned meaning; the compounds of the formula (V) may be cyclized and reacted with a compound of the formula

R''Z, (VII)

wherein

Z is a radical which is easily removed, for example halogen.

This method is illustrated by the following formula scheme:

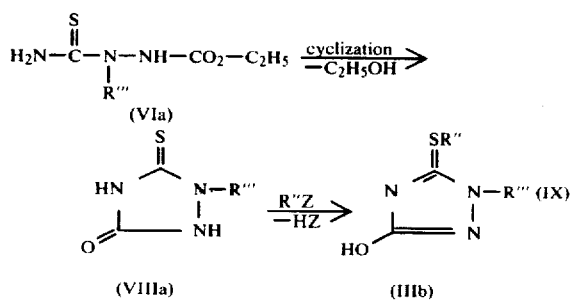

(b) If X represents oxygen, chloroformic acid ethyl ester may be reacted with potassium thiocyanate and subsequently with an alcohol to give a compound of the general formula

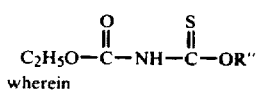
(X)

wherein

R'' has the abovementioned meaning, and this intermediate product may be cyclized in the presence of a hydrazine derivative in accordance with the following reaction scheme:

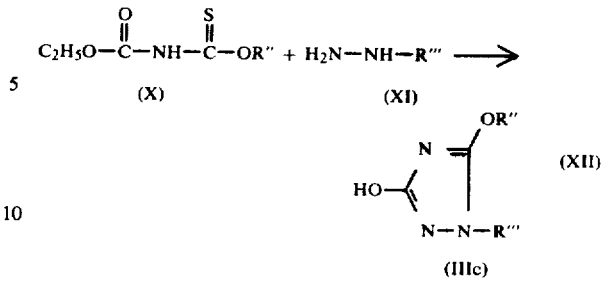

The following may be mentioned individually as examples of triazolyl derivatives (III) to be used in the process of the invention: 1-methyl-, 1-ethyl-, 1-n-propyl- and 1-iso-propyl-3-hydroxy-5-methoxytriazole-(1,2,4) and also the corresponding -5-ethoxy-, -5-n-propoxy-, -5-isopropoxy-, 5-methylthio-, -5-ethylthio, -5-n-propylthio-, -5-iso-propylthio-, -5-allyloxy-, -5-allylthio-, -5-cyanomethyloxy- and -5-cyanomethylthio derivatives.

The process of the invention is preferably carried out with the use of a solvent, which term includes a mere diluent. Practically all inert organic solvents can be used for this purpose. These in particular include optionally chlorinated aliphatic and aromatic hydrocarbons, e.g. benzene, toluene, xylene, benzine, methylene chloride, chloroform, carbon tetrachloride and chlorobenzene; ethers, e.g. diethyl ether, dibutyl ether and dioxane; ketones, e.g. acetone, methyl ethyl ketone, methyl isopropyl ketone and methyl isobutyl ketone; and nitriles, e.g. acetonitrile and propionitrile.

All customary acid-binding agents can be used as acid acceptors. Alkali metal carbonates and alkali metal alcoholates, such as sodium carbonate and potassium carbonate, sodium methylate and ethylate and potassium methylate and ethylate, and also aliphatic, aromatic or heterocyclic amines, especially triethylamine, dimethylamine, dimethylaniline, dimethylbenzylamine and pyridine, have proved particularly suitable.

The reaction temperature can be varied over a wide range. In general, the reaction is carried out at 0° to 120° C., preferably at 20° to 70° C. It is allowed in general to take place under normal pressure.

To carry out the process, the starting compounds are generally employed in equimolar ratios. An excess of one or other component in general does not appear to result in any significant advantage. The reaction is preferably carried out in the presence of one of the abovementioned solvents, optionally in the presence of an acid acceptor, at the indicated temperatures. After a reaction time of one or more hours, in most cases at raised temperatures, the batch may be cooled and the reaction mixture poured into water and taken up in an organic solvent, for example benzene. Thereafter, the mixture may be worked up in the usual manner by drying the organic phase, evaporating the solvent and optionally distilling the residue.

Most of the new compounds are obtained in the form of oils which in some cases can not be distilled without decomposition but can be freed of the last volatile constituents by so-called "slight distillation", that is to say prolonged heating under reduced pressure to moderately elevated temperatures, and they can in this way be purified. They are characterized, above all, by the refractive index.

The O-triazolylthionophosphoric(phosphonic) acid esters and ester-amides according to the invention are distinguished by an excellent insecticidal, especially soil-insecticidal, and acaricidal activity against plant pests, hygiene pests and pests of stored products and, in the veterinary medicine field, by an excellent activity against animal ectoparasites, such as parasitic fly larvae and ticks. They couple a low phytotoxicity with a good action both against biting and against sucking insects.

For this reason, the compounds according to the invention can be employed successfully as pesticides in plant protection and in the hygiene field, the field of protection of stored products and the veterinary field.

To the sucking insects there belong, in the main, aphids (Aphidae) such as the green peach aphid (*Myzus persicae*), the bean aphid (*Doralis fabae*), the bird cherry aphid (*Rhopalosiphum padi*), the pea aphid (*Macrosiphum pisi*) and the potato aphid (*Macrosiphum solanifolii*), the current gall aphid (*Cryptomyzus korschelti*), the rosy apple aphid (*Sappaphis mali*), the mealy plum aphid (*Hyalopterus arundinis*) and the cherry black-fly (*Myzus cerasi*); in addition, scales and mealybugs (Coccina), for example the oleander scale (*Aspidiotus hederae*) and the soft scale (*Lecanium hesperidum*) as well as the grape mealybug (*Pseudococcus maritimus*); thrips (Thysanoptera), such as *Hercinothrips femoralis*, and bugs, for example the beet bug (*Piesma quadrata*), the red cotton bug (*Dysdercus intermedius*), the red bug (*Cimex lectularius*), the assassin bug (*Rhodnius prolixus*) and Chagas' bug (*Triatoma infestans*) and, further, cicadas, such as *Euscelis bilobatus* and *Nephotettix bipunctatus*.

In the case of the biting insects, above all there should be mentioned butterfly caterpillars (Lepidoptera) such as the diamond-back moth (*Plutella maculipennis*), the gypsy moth (*Lymantria dispar*), the brown-tail moth (*Euproctis chrysorrhoea*) and tent caterpillar (*Malacosoma neustria*); further, the cabbage moth (*Mamestra brassicae*) and the cutworm (*Agrotis segetum*), the large white butterfly (*Pieris brassicae*), the small winter moth (*Cheimatobia brumata*), the green oak tortrix moth (*Tortrix viridana*), the fall armyworm (*Laphygma frugiperda*) and cotton worm (*Prodenia litura*), the ermine moth (*Hyponomeuta padella*), the Mediterranean flour moth (*Sphestia kuhniella*) and greater wax moth (Galleria mellonella).

Also to be classed with the biting insects are beetles (Coleoptera), for example the granary weevil (*Sitophilus granarius=Calandra granaria*), the Colorado beetle (*Leptinotarsa decemlineata*), the dock beetle (*Gastrophysa viridula*), the mustard beetle (*Phaedon cochleariae*), the blossom beetle (*Meligethes aeneus*), the raspberry beetle (*Byturus tomentosus*), the bean weevil (*Bruchidius=Acanthoscelides obtectus*), the leather beetle (*Dermestes frischi*), the khapra beetle (*Trogoderma granarium*), the flour beetle (*Tribolium castaneum*), the northern corn billbug (*Calandra* or *Sitophilus zeamais*), the drugstore beetle (*Stegobium paniceum*), the yellow mealworm (*Tenebrio molitor*) and the saw-toothed grain beetle (*Oryzaephilus surinamensis*), and also species living in the soil, for example wireworms (Agriotes spec.) and larvae of the cockchafer (*Melolontha melolontha*); cockroaches, such as the German cockroach (*Biattella germanica*), American cockroach (*Priplaneta americana*), Madeira cockroach (*leucophaea* or *Rhyparobia maderae*), oriental cockroach (*Blatta orientalis*), the giant cockroach (*Blaberus giganteus*) and the black giant cockroach (*Blaberus fuscus*) as well as *Henschoutedenia flexivitta*; further, Orthoptera, for example the house cricket (*Gryllus domesticus*); termites such as the eastern subterranean termite (*Reticulitermes flavipes*) and Hymenoptera such as ants, for example the garden ant (*Lasius niger*).

The Diptera comprise essentially the flies, such as the vinegar fly (*Dresephila melanogaster*), the Mediterranean fruit fly (*Ceratitis capitata*), the house fly (*Musca domestica*), the little house fly (*Farnia canicularis*), the black blow fly (*Phormia regina*) and bluebottle fly (*Calliphora erythrocephala*) as well as the stable fly (*Stomoxys calcitrans*); further, gnats, for example mosquitoes such as the yellow fever mosquito (*Aedes aegypti*), the northern house mosquito (*Culex pipiens*) and the malaria mosquito (*Anopheles stephensi*).

With the mites (*Acari*) there are classed, in particular, the spider mites (Tetranychidae) such as the two-spotted spider mite (*Tetranychus urticae*) and the European red mite (*Paratetranychus pilosus=Panonychus ulmi*), gall mites, for example the blackcurrent gall mite (*Eriophyes ribis*) and tarsonemids, for example the broad mite (*Hemitarsonemus latus*) and the cyclamen mite (*Tarsonemus pallidus*); finally, ticks, such as the relapsing fever tick (*Ornithodorus moubata*).

When applied against hygiene pests and pests of stored products, particularly flies and mosquitoes, the products are also distinguished by an outstanding residual activity on wood and clay, as well as a good stability to alkali on limed substrates.

The active compounds according to the instant invention can be utilized, if desired, in the form of the usual formulations or compositions with conventional inert (i.e. plant compatible or herbicidally inert) pesticide diluents or extenders, i.e. diluents, carriers or extenders of the type usable in conventional pesticide formulations or compositions, e.g. conventional pesticide dispersible carrier vehicles such as gases, solutions, emulsions, suspensions, emulsifiable concentrates, spray powders, pastes, soluble powders, dusting agents, granules, etc. These are prepared in known manner, for instance by extending the active compounds with conventional pesticide dispersible liquid diluent carriers and/or dispersible solid carriers optionally with the use of carrier vehicle assistants, e.g. conventional pesticide surface-active agents, including emulsifying agents and-/or dispersing agents, whereby, for example, in the case where water is used as diluent, organic solvents may be added as auxiliary solvents. The following may be chiefly considered for use as conventional carrier vehicles for this purpose: aerosol propellants which are gaseous at normal temperatures and pressures, such as freon; inert dispersible liquid diluent carriers, including inert organic solvents, such as aromatic hydrocarbons (e.g. benzene, toluene, xylene, alkyl naphthalenes, etc.), halogenated, especially chlorinated, aromatic hydrocarbons (e.g. chlorobenzenes, etc.), cycloalkanes (e.g. cyclohexane, etc.), paraffins (e.g. petroleum or mineral oil fractions), chlorinated aliphatic hydrocarbons (e.g. methylene chloride, chloroethylenes, etc.), alcohols (e.g. methanol, ethanol, propanol, butanol, glycol, etc.) as well as ethers and esters thereof (e.g. glycol monomethyl ether, etc.), amines (e.g. ethanolamine, etc.), amides (e.g. dimethyl formamide, etc.), sulfoxides (e.g. dimethyl sulfoxide, etc.), acetonitrile, ketones (e.g. acetone, methyl ethyl ketone, methyl isobutyl ketone, cyclohexanone, etc.), and/or water; as well as inert dispersible finely divided solid carriers, such as ground natural minerals (e.g. kaolins, clays, alumina, silica, chalk, i.e. calcium carbonate, talc, attapulgite, montmorillonite, kieselguhr, etc.) and ground synthetic minerals (e.g. highly dispersed silicic acid, silicates, e.g. alkali silicates, etc.); whereas the following may be chiefly considered for use as conventional carrier vehicle assistants, e.g. surface-active agents, for this purpose: emulsifying agents, such as non-ionic and/or anionic emulsifying agents (e.g. polyethylene oxide esters of fatty acids, polyethylene oxide ethers of fatty alcohols, alkyl sulfates, alkyl sulfonates, aryl sulfonates, albumin hydrolyzates, etc., and especially alkyl arylpolyglycol ethers, magnesium stearate, sodium oleate, etc.); and/or dispersing agents, such as lignin, sulfite waste liquors, methyl cellulose, etc.

Such active compounds may be employed alone or in the form of mixtures with one another and/or with such solid and/or liquid dispersible carrier vehicles and/or with other known compatible active agents, especially plant protection agents, such as other insecticides or acaricides, and fungicides, bactericides, rodenticides, nematocides, herbicides, fertilizers, growth-regulating agents, etc. if desired, or in the form of particular dosage preparations for specific application made therefrom, such as solutions, emulsions, suspensions, powders, pastes and granules, which are thus ready for use.

As concerns commercially marketed preparations, these generally contemplate carrier composition mixtures in which the active compound is present in an amount substantially between about 0.1–95% by weight, and preferably 0.5–90% by weight, of the mixture, whereas carrier composition mixtures suitable for direct application or field application generally contemplate those in which the active compound is present in an amount substantially between about 0.0001–10%, preferably 0.01–1%, by weight of the mixture. Thus, the present invention contemplates over-all compositions which comprises mixture of a conventional dispersible carrier vehicle such as (1) a dispersible inert finely divided carrier solid, and/or (2) a dispersible carrier liquid such as an inert organic solvent and/or water preferably including a surface-active effective amount of a carrier vehicle assistant, e.g. a surface-active agent, such as an emulsifying agent and/or a dispersing agent, and an amount of the active compound which is effective for the purpose in question and which is generally between about 0.0001–95%, and preferably 0.01–95%, by weight of the mixture.

The active compounds can also be used in accordance with the well known ultra-low-volume process with good success, i.e. by applying such compound if normally a liquid, or by applying a liquid composition containing the same, via very effective atomizing equipment, in finely divided form, e.g. average particle diameter of from 50–100 microns, or even less, i.e. mist form, for example by airplane crop spraying techniques. Only up to at most about a few liters/hectare are needed, and often amounts only up to about 15 to 1000 g/hectare, preferably 40 to 600 g/hectare, are sufficient. In this process it is possible to use highly concentrated liquid compositions with said liquid carrier vehicles containing from about 20 to about 95% by weight of the active compound or even the 100% active substance alone, e.g. about 20–100% by weight of the active compound.

Furthermore, the present invention contemplates methods of selectively killing, combating or controlling pests, e.g. insects and acarids, which comprises applying to at least one of correspondingly (a) such insects, (b) such acarids, and (c) the corresponding habitat thereof, i.e. the locus to be protected, a correspondingly combative or toxic amount, i.e. an insecticidally or acaricidally effective amount, of the particular active compound of the invention alone or together with a carrier vehicle as noted above. The instant formations or compositions are applied in the usual manner, for instance by spraying, atomizing, vaporizing, scattering, dusting, watering, squirting, sprinkling, pouring, fumigating, dressing, encrusting, and the like.

It will be realized, of course, that the concentration of the particular active compound utilized in admixture with the carrier vehicle will depend upon the intended application. Therefore, in special cases it is possible to go above or below the aforementioned concentration ranges.

The synthesis, unexpected superiority and outstanding activity of the particular new compounds of the present invention are illustrated, without limitation, by the following examples:

EXAMPLE 1

Phaedon larvae test

Solvent: 3 parts by weight of acetone

Emulsifier: 1 part by weight of alkylaryl polyglycol ether

To produce a suitable preparation of active compound, 1 part by weight of the active compound was mixed with the stated amount of solvent containing the stated amount of emulsifier and the concentrate was diluted with water to the desired concentration.

Cabbage plants (*Brassica oleracea*) were sprayed with the preparation of the active compound until dripping wet and were then infested with mustard beetle larvae (*Phaedon cochleariae*).

After the specified periods of time, the degree of destruction was determined in %: 100% means that all beetle larvae were killed whereas 0% means that none of the beetle larvae were killed.

The active compounds, the concentrations of the active compounds, the evaluation times and the results can be seen from the following Table 1:

TABLE 1

(Phaedon larvae test)

| Active compound | Active compound concentration in % by weight | Degree of destruction in % after 3 days |
|---|---|---|
| (A) (known) $(CH_3O)_2\overset{S}{\overset{\|}{P}}-O-C(=CH-C(CH_3)=N-NH-)$ (pyrazole) | 0.1 | 0 |
| (1) $(CH_3O)_2\overset{S}{\overset{\|}{P}}-O-C(SCH_3)=N-N(CH_3)-N=C(CH_3)-$ | 0.1<br>0.01 | 100<br>100 |
| (8) $(CH_3O)_2\overset{S}{\overset{\|}{P}}-O-C(SCH_3)=N-N(C_2H_5)-N=C(CH_3)-$ | 0.1<br>0.01 | 100<br>100 |
| (4) $(CH_3O)_2\overset{S}{\overset{\|}{P}}-O-C(SCH_3)=N-N(C_3H_7\text{-}i)-N=C(CH_3)-$ | 0.1<br>0.01<br>0.001 | 100<br>100<br>100 |
| (2) $(C_2H_5O)_2\overset{S}{\overset{\|}{P}}-O-C(SCH_3)=N-N(CH_3)-N=C(CH_3)-$ | 0.1<br>0.01 | 100<br>100 |
| (7) $(C_2H_5O)_2\overset{S}{\overset{\|}{P}}-O-C(SCH_3)=N-N(C_2H_5)-N=C(CH_3)-$ | 0.1<br>0.01<br>0.001 | 100<br>100<br>90 |
| (13) $(C_2H_5O)_2\overset{S}{\overset{\|}{P}}-O-C(SCH_3)=N-N(C_3H_7\text{-}i)-N=C(CH_3)-$ | 0.1<br>0.01<br>0.001 | 100<br>100<br>95 |
| (12) $(C_2H_5O)_2\overset{S}{\overset{\|}{P}}-O-C(OCH_3)=N-N(CH_3)-N=C(CH_3)-$ | 0.1<br>0.01 | 100<br>100 |
| (3) $(C_2H_5O)_2\overset{S}{\overset{\|}{P}}-O-C(OC_2H_5)=N-N(CH_3)-N=C(CH_3)-$ | 0.1<br>0.01 | 100<br>100 |

TABLE 1-continued (Phaedon larvae test)

| Active compound | Active compound concentration in % by weight | Degree of destruction in % after 3 days |
|---|---|---|
| (10) $(C_2H_5O)_2\overset{S}{\underset{\|}{P}}-O-C(\text{S-CH}_2\text{-CN})=N-N(C_2H_5)$ | 0.1<br>0.01 | 100<br>100 |
| (9) $(C_2H_5O)_2\overset{S}{\underset{\|}{P}}-O-C(\text{S-CH}_2\text{-CH=CH}_2)=N-N(C_2H_5)$ | 0.1<br>0.01 | 100<br>100 |
| (6) $C_6H_5,C_2H_5O$-$\overset{S}{\underset{\|}{P}}$-$O-C(SCH_3)=N-N(C_3H_7\text{-}i)$ | 0.1<br>0.01<br>0.001 | 100<br>100<br>90 |
| (5) $i\text{-}C_3H_7\text{-}NH, C_2H_5O$-$\overset{S}{\underset{\|}{P}}$-$O-C(SCH_3)=N-N(C_3H_7\text{-}i)$ | 0.1<br>0.01 | 100<br>100 |
| (14) $C_2H_5O, C_2H_5$-$\overset{S}{\underset{\|}{P}}$-$O-C(SCH_3)=N-N(C_2H_5)$ | 0.1<br>0.01<br>0.001 | 100<br>100<br>100 |
| (16) $C_3H_7O, CH_3O$-$\overset{S}{\underset{\|}{P}}$-$O-C(SCH_3)=N-N(C_3H_7i)$ | 0.1<br>0.01<br>0.001 | 100<br>100<br>100 |
| (15) $C_3H_7O, C_2H_5O$-$\overset{S}{\underset{\|}{P}}$-$O-C(SCH_3)=N-N(C_3H_7i)$ | 0.1<br>0.01<br>0.001 | 100<br>100<br>100 |

EXAMPLE 2

Plutella test

Solvent: 3 parts by weight of acetone

Emulsifier: 1 part by weight of alkylaryl polyglycol ether

To produce a suitable preparation of active compound, 1 part by weight of the active compound was mixed with the stated amount of solvent containing the stated amount of emulsifier and the concentrate was diluted with water to the desired concentration.

Cabbage leaves (*Brassica oleracea*) were sprayed with the preparation of the active compound until dew moist and were then infested with caterpillars of the diamond-back moth (*Plutella maculipennis*).

After the specified periods of time, the degree of destruction was determined as a percentage: 100% means that all the caterpillars were killed whereas 0% means that none of the caterpillars were killed.

The active compounds, the concentrations of the active compounds, the evaluation times and the results can be seen from the following Table 2:

TABLE 2

(Plutella test)

| Active compound | Active compound concentration in % by weight | Degree of destruction in % after 3 days |
|---|---|---|
| (A) (known) (CH₃O)₂P(S)—O—C(=CH—C(CH₃)=N—NH) | 0.1 | 0 |
| (1) (CH₃O)₂P(S)—O—C(SCH₃)=... N—N(CH₃) | 0.1<br>0.01 | 100<br>100 |
| (8) (CH₃O)₂P(S)—O—C(SCH₃)=... N—N(C₂H₅) | 0.1<br>0.01<br>0.001 | 100<br>100<br>95 |
| (4) (CH₃O)₂P(S)—O—C(SCH₃)=... N—N(C₃H₇-i) | 0.1<br>0.01<br>0.001 | 100<br>100<br>95 |
| (2) (C₂H₅O)₂P(S)—O—C(SCH₃)=... N—N(CH₃) | 0.1<br>0.01<br>0.001 | 100<br>100<br>75 |
| (7) (C₂H₅O)₂P(S)—O—C(SCH₃)=... N—N(C₂H₅) | 0.1<br>0.01<br>0.001 | 100<br>100<br>100 |
| (13) (C₂H₅O)₂P(S)—O—C(SCH₃)=... N—N(C₃H₇-i) | 0.1<br>0.01<br>0.001 | 100<br>100<br>100 |
| (12) (C₂H₅O)₂P(S)—O—C(OCH₃)=... N—N(CH₃) | 0.1<br>0.01 | 100<br>100 |
| (3) (C₂H₅O)₂P(S)—O—C(OC₂H₅)=... N—N(CH₃) | 0.1<br>0.01 | 100<br>100 |

TABLE 2-continued (Plutella test)

| Active compound | Active compound concentration in % by weight | Degree of destruction in % after 3 days |
|---|---|---|
| (10) [(C$_2$H$_5$O)$_2$P(S)−O−C(=N−N(C$_2$H$_5$))−SCH$_2$−CN on heterocycle] | 0.1<br>0.01 | 100<br>100 |
| (9) [(C$_2$H$_5$O)$_2$P(S)−O−C(=N−N(C$_2$H$_5$))−S−CH$_2$−CH=CH$_2$] | 0.1<br>0.01<br>0.001 | 100<br>100<br>50 |
| (11) [C$_6$H$_5$−P(S)(OC$_2$H$_5$)−O−C(=N−N(CH$_3$))−OCH$_3$] | 0.1<br>0.01 | 100<br>100 |
| (6) [C$_6$H$_5$−P(S)(OC$_2$H$_5$)−O−C(=N−N(C$_3$H$_7$-i))−SCH$_3$] | 0.1<br>0.01<br>0.001 | 100<br>100<br>95 |
| (5) [i-C$_3$H$_7$−NH−P(S)(OC$_2$H$_5$)−O−C(=N−N(C$_3$H$_7$-i))−SCH$_3$] | 0.1<br>0.01 | 100<br>100 |
| (14) [C$_2$H$_5$O−P(S)(C$_2$H$_5$)−O−C(=N−N(C$_2$H$_5$))−SCH$_3$] | 0.1<br>0.01<br>0.001 | 100<br>100<br>50 |
| (16) [C$_3$H$_7$O−P(S)(CH$_3$O)−O−C(=N−N(C$_3$H$_7$i))−SCH$_3$] | 0.1<br>0.01<br>0.001 | 100<br>100<br>85 |
| (15) [C$_3$H$_7$O−P(S)(C$_2$H$_5$O)−O−C(=N−N(C$_3$H$_7$i))−SCH$_3$] | 0.1<br>0.01<br>0.001 | 100<br>100<br>100 |

EXAMPLE 3

Myzus test (contact action)
Solvent: 3 parts by weight of acetone
Emulsifier: 1 part by weight of alkylaryl polyglycol ether To produce a suitable preparation of active compound, 1 part by weight of the active compound was mixed with the stated amount of solvent containing the stated amount of emulsifier and the concentrate was diluted with water to the desired concentration.

Cabbage plants (*Brassica oleracea*) which had been heavily infested with peach aphids (*Myzus persicae*) were sprayed with the preparation of the active compound until dripping wet.

After the specified periods of time, the degree of destruction was determined as a percentage: 100% means that all the aphids were killed whereas 0% means that none of the aphids were killed.

The active compounds, the concentrations of the active compounds, the evaluation times and the results can be seen from the following Table 3:

TABLE 3

(Kyzus test)

| Active compound | Active compound concentration in % by weight | Degree of destruction in % after 1 day |
|---|---|---|
| (CH$_3$O)$_2$P(S)−O−C(CH$_3$)=CH−N(H)−N= (A) (known) | 0.1 | 0 |
| (C$_2$H$_5$O)$_2$P(S)−O−C(CH$_3$)=CH−N(H)−N= (B) (known) | 0.1<br>0.01<br>0.001 | 99<br>40<br>0 |
| (CH$_3$O)$_2$P(S)−O−C(SCH$_3$)=N−N(CH$_3$)−CH$_3$ (1) | 0.1<br>0.01<br>0.001 | 100<br>100<br>100 |
| (CH$_3$O)$_2$P(S)−O−C(SCH$_3$)=N−N(CH$_3$)−C$_2$H$_5$ (8) | 0.1<br>0.01<br>0.001<br>0.0001 | 100<br>100<br>99<br>30 |
| (CH$_3$O)$_2$P(S)−O−C(SCH$_3$)=N−N(CH$_3$)−C$_3$H$_7$-i (4) | 0.1<br>0.01<br>0.001<br>0.0001 | 100<br>100<br>100<br>90 |
| (C$_2$H$_5$O)$_2$P(S)−O−C(SCH$_3$)=N−N(CH$_3$)−CH$_3$ (2) | 0.1<br>0.01<br>0.001 | 100<br>100<br>98 |
| (C$_2$H$_5$O)$_2$P(S)−O−C(SCH$_3$)=N−N(CH$_3$)−C$_2$H$_5$ (7) | 0.1<br>0.01<br>0.001<br>0.0001 | 100<br>100<br>100<br>80 |
| (C$_2$H$_5$O)$_2$P(S)−O−C(SCH$_3$)=N−N(CH$_3$)−C$_3$H$_7$-i (13) | 0.1<br>0.01<br>0.001 | 100<br>100<br>100 |
| (C$_2$H$_5$O)$_2$P(S)−O−C(OCH$_3$)=N−N(CH$_3$)−CH$_3$ (12) | 0.1<br>0.01<br>0.001 | 100<br>100<br>97 |

TABLE 3-continued
(Kyzus test)

| Active compound | Active compound concentration in % by weight | Degree of destruction in % after 1 day |
|---|---|---|
| (3) 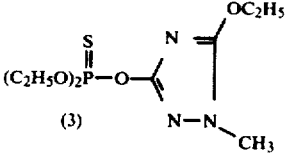 | 0.1<br>0.01<br>0.001 | 100<br>100<br>45 |
| (10) 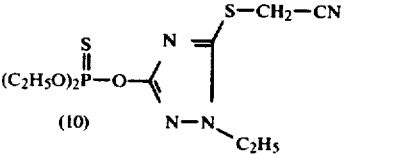 | 0.1<br>0.01<br>0.001 | 100<br>100<br>100 |
| (9) 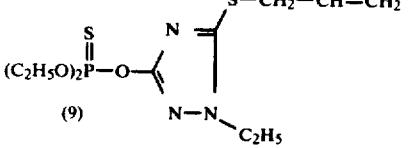 | 0.1<br>0.01<br>0.001 | 100<br>100<br>99 |
| (6) 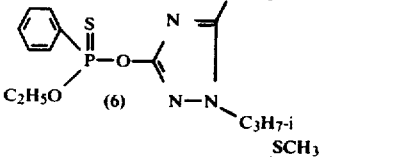 | 0.1<br>0.01<br>0.001 | 100<br>100<br>99 |
| (5) 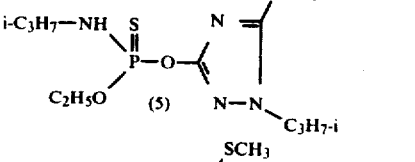 | 0.1<br>0.01<br>0.001 | 100<br>100<br>99 |
| (14) 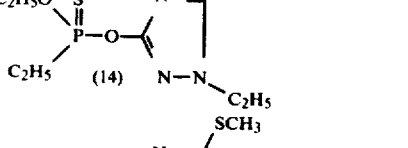 | 0.1<br>0.01<br>0.001 | 100<br>100<br>100 |
| (16) 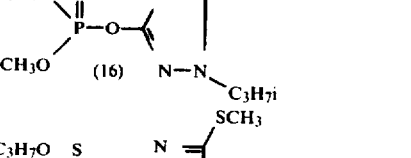 | 0.1<br>0.01<br>0.001<br>0.0001 | 100<br>100<br>100<br>80 |
| (15) 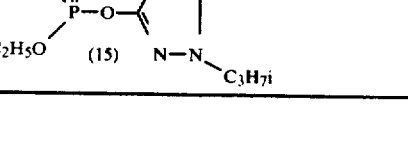 | 0.1<br>0.01<br>0.001<br>0.0001 | 100<br>100<br>100<br>60 |

EXAMPLE 4

Critical concentration test/soil insects
Test insect: Tenebrio molitor
Solvent: 3 parts by weight of acetone
Emulsifier: 1 part by weight of alkylaryl polyglycol ether To produce a suitable preparation of active compound, 1 part by weight compound was mixed with the stated amount of solvent, the stated amount of emulsifier was added and the concentrate was diluted with water to the desired concentration.

The preparation of active compound was intimately mixed with soil. The concentration of the active compound in the preparation was of practically no importance; only the amount by weight of active compound per unit volume of soil, which is given in ppm (mg/l) was decisive. The soil was filled into pots and the pots were left to stand at room temperature. After 24 hours, the test animals were introduced into the treated soil and after a further 48 hours the degree of effectiveness of the active compound was determined in % by counting the dead and live test insects. The degree of destruction was 100% if all test insects were killed and was 0% if just as many test insects were still alive as in the case of the control.

The active compounds, the amounts used and the results can be seen from Table 4 which follows:

TABLE 4

Critical concentration test/soil insecticides
(*Tenebrio molitor*)

| Active compound | Degree of destruction in % at an active compound concentration of ppm | | | | |
|---|---|---|---|---|---|
| | 20 | 10 | 5 | 2.5 | 1.25 |
| (A) (known) $(CH_3O)_2P(S)$—O—pyrazolyl-CH$_3$ | 0 | | | | |
| (B) (known) $(C_2H_5O)_2P(S)$—O—pyrazolyl-CH$_3$ | 0 | | | | |
| (13) $(C_2H_5O)_2P(S)$—O—C(SCH$_3$)=N—N(C$_3$H$_7$-i) | 100 | 100 | 100 | 100 | 90 |
| (2) $(C_2H_5O)_2P(S)$—O—C(SCH$_3$)=N—N(CH$_3$) | 100 | 100 | 100 | 95 | 50 |
| (5) (i-C$_3$H$_7$-NH)(C$_2$H$_5$O)P(S)—O—C(SCH$_3$)=N—N(C$_3$H$_7$-i) | 100 | 50 | 0 | | |
| (6) (C$_6$H$_5$)(C$_2$H$_5$O)P(S)—O—C(SCH$_3$)=N—N(C$_3$H$_7$-i) | 100 | 100 | 80 | | |
| (4) $(CH_3O)_2P(S)$—O—C(SCH$_3$)=N—N(C$_3$H$_7$-i) | 100 | 100 | 100 | 95 | 20 |
| (9) $(C_2H_5O)_2P(S)$—O—C(S—CH$_2$—CH=CH$_2$)=N—N(C$_2$H$_5$) | 100 | 100 | 95 | 50 | |
| (7) $(C_2H_5O)_2P(S)$—O—C(SCH$_3$)=N—N(C$_2$H$_5$) | 100 | 100 | 100 | 95 | 50 |

TABLE 4-continued

Critical concentration test/soil
insecticides
(*Tenebrio molitor*)

| Active compound | Degree of destruction in % at an active compound concentration of ppm | | | | |
|---|---|---|---|---|---|
| | 20 | 10 | 5 | 2.5 | 1.25 |
| (CH$_3$O)$_2$P(S)—O—C(=N–N(C$_2$H$_5$))—C(CH$_3$)=N—SCH$_3$ (8) | 100 | 100 | 50 | | |

EXAMPLE 5

Tetranychus test

Solvent: 3 parts by weight of acetone

Emulsifier: 1 part by weight of alkylaryl polyglycol ether

To produce a suitable preparation of active compound, 1 part by weight of the active compound was mixed with the stated amount of solvent containing the stated amount of emulsifier and the concentrate so obtained was diluted with water to the desired concentration.

Bean plants (*Phaseolus vulgaris*), which had a height of approximately 10–30 cm, were sprayed with the preparation of the active compound until dripping wet. These bean plants were heavily infested with the two-spotted spider mite (*Tetranychus urticae*) in all stages of development.

After the specified periods of time, the effectiveness of the preparation of active compound was determined by counting the dead mites. The degree of destruction thus obtained was expressed as a percentage: 100% means that all the spider mites were killed whereas 0% means that none of the spider mites were killed.

The active compounds, the concentrations of the active compounds, the evaluation times and the results can be seen from the following Table 5:

TABLE 5

(Tetranychus test)

| Active compound | Active compound concentration in % by weight | Degree of destruction in % after 2 days |
|---|---|---|
| (CH$_3$O)$_2$P(S)—O—C(CH$_3$)=CH—N=N—H (known) (A) | 0.1 | 0 |
| (C$_2$H$_5$O)$_2$P(S)—O—C(CH$_3$)=CH—N=N—H (known) (B) | 0.1<br>0.01 | 50<br>0 |
| (CH$_3$O)$_2$P(S)—O—C(=N–N(CH$_3$))—C(CH$_3$)=N—SCH$_3$ (1) | 0.1<br>0.01 | 98<br>95 |
| (CH$_3$O)$_2$P(S)—O—C(=N–N(C$_2$H$_5$))—C(CH$_3$)=N—SCH$_3$ (8) | 0.1<br>0.01 | 100<br>100 |

TABLE 5-continued
(Tetranychus test)
| Active compound | Active compound concentration in % by weight | Degree of destruction in % after 2 days |
|---|---|---|
| 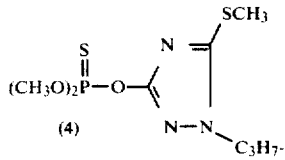 (4) | 0.1<br>0.01<br>0.001 | 100<br>100<br>95 |
| 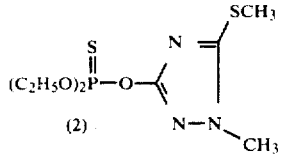 (2) | 0.1<br>0.01<br>0.001 | 100<br>98<br>95 |
| 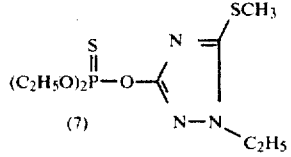 (7) | 0.1<br>0.01<br>0.001 | 100<br>100<br>50 |
| 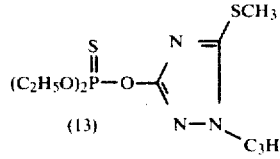 (13) | 0.1<br>0.01<br>0.001 | 100<br>100<br>60 |
| 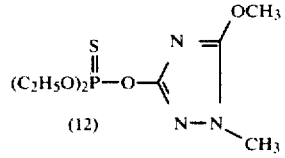 (12) | 0.1<br>0.01<br>0.001 | 100<br>99<br>70 |
| 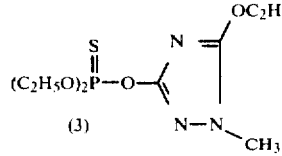 (3) | 0.1<br>0.01 | 100<br>50 |
| 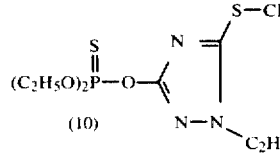 (10) | 0.1<br>0.01 | 100<br>90 |
| 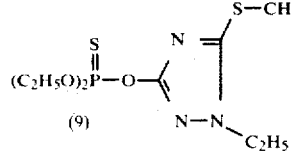 (9) | 0.1<br>0.01 | 100<br>100 |
| 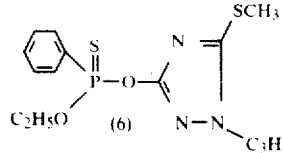 (6) | 0.1<br>0.01<br>0.001 | 100<br>98<br>65 |

TABLE 5-continued (Tetranychus test)

| Active compound | Active compound concentration in % by weight | Degree of destruction in % after 2 days |
|---|---|---|
| i-$C_3H_7$—NH—P(=S)(—O$C_2H_5$)—O—C(SCH$_3$)=N—N(C$_3$H$_7$-i) ring (5) | 0.1<br>0.01<br>0.001 | 100<br>100<br>30 |
| $C_2H_5O$—P(=S)(—$C_2H_5$)—O—C(SCH$_3$)=N—N($C_2H_5$) ring (14) | 0.1<br>0.01<br>0.001 | 100<br>100<br>90 |
| $C_3H_7O$—P(=S)(—O$CH_3$)—O—C(SCH$_3$)=N—N(C$_3$H$_7$i) ring (16) | 0.1<br>0.01<br>0.001<br>0.0001 | 100<br>100<br>99<br>40 |
| $C_3H_7O$—P(=S)(—O$C_2H_5$)—O—C(SCH$_3$)=N—N(C$_3$H$_7$i) ring (15) | 0.1<br>0.01<br>0.001 | 100<br>100<br>75 |

EXAMPLE 6

LD$_{100}$ test
Test insects: *Sitophilus granarius*
Solvent: Acetone 2 parts by weight of the active compound were dissolved in 1,000 parts by volume of the solvent. The solution so obtained was diluted with further solvent to the desired concentration.

2.5 ml of the solution of the active compound were pipetted into a Petri dish. On the bottom of the Petri dish there was a filter paper with a diameter of about 9.5 cm. The Petri dish remained uncovered until the solvent had completely evaporated. The amount of active compound per m² of filter paper varied with the concentration of the solution of active compound. About 25 test insects were then placed in the Petri dish and it was covered with a glass lid.

The condition of the test insects was observed 3 days after the commencement of the experiments. The destruction, in %, was determined.

The active compounds, the concentrations of the active compounds, the test insects and the results can be seen from the following Table 6:

TABLE 6

(LD$_{100}$ test/*Sitophilus granarius*)

| Active compound | Active compound concentration of the solution in % by weight | Degree of destruction in % |
|---|---|---|
| ($C_2H_5O$)$_2$—P(=S)—O—C(CH$_3$)=CH—ring with N—N—H (known) (B) | 0.2<br>0.02 | 100<br>0 |
| (CH$_3$O)$_2$—P(=S)—O—C(CH$_3$)=CH—ring with N—N—H (known) (A) | 0.2 | 0 |
| ($C_2H_5O$)$_2$—P(=S)—O—C(OC$_2$H$_5$)=N—ring with N—N—CH$_3$ (3) | 0.2<br>0.02<br>0.002 | 100<br>100<br>0 |
| ($C_2H_5O$)$_2$—P(=S)—O—C(SCH$_3$)=N—ring with N—N—C$_3$H$_7$-i (13) | 0.2<br>0.02<br>0.002<br>0.0002 | 100<br>100<br>100<br>0 |

TABLE 6-continued (LD$_{100}$ test/*Sitophilus granarius*)

| Active compound | Active compound concentration of the solution in % by weight | Degree of destruction in % |
|---|---|---|
| (C$_2$H$_5$O)$_2$—P(=S)—O—C(SCH$_3$)=N—N(CH$_3$)—N= (2) | 0.2<br>0.02<br>0.002 | 100<br>100<br>70 |
| (CH$_3$O)$_2$—P(=S)—O—C(SCH$_3$)=N—N(CH$_3$)—N= (1) | 0.2<br>0.02<br>0.002<br>0.0002 | 100<br>100<br>100<br>0 |
| (C$_2$H$_5$O)$_2$—P(=S)—O—C(OCH$_3$)=N—N(CH$_3$)—N= (12) | 0.2<br>0.02<br>0.002 | 100<br>100<br>0 |
| i-C$_3$H$_7$—NH—P(=S)(C$_2$H$_5$O)—O—C(SCH$_3$)=N—N(C$_3$H$_7$-i)—N= (5) | 0.2<br>0.02<br>0.002 | 100<br>100<br>0 |
| C$_6$H$_5$—P(=S)(C$_2$H$_5$O)—O—C(SCH$_3$)=N—N(C$_3$H$_7$-i)—N= (6) | 0.2<br>0.02<br>0.002 | 100<br>100<br>70 |
| (CH$_3$O)$_2$—P(=S)—O—C(SCH$_3$)=N—N(C$_3$H$_7$-i)—N= (4) | 0.2<br>0.02<br>0.002<br>0.0002 | 100<br>100<br>100<br>0 |

EXAMPLE 7

LT$_{100}$ test for Diptera
Test insects: *Musca domestica*
Solvent: Acetone 2 parts by weight of active compound were dissolved in 1,000 parts by volume of solvent. The solution so obtained was diluted with further solvent to the desired lower concentrations.

2.5 ml of the solution of active compound were pipetted into a Petri dish. On the bottom of the Petri dish there was a filter paper with a diameter of about 9.5 cm. The Petri dish remained uncovered until the solvent had completely evaporated. The amount of active compound per m$^2$ of filter paper varied with the concentration of the solution of active compound. About 25 test insects were then placed in the Petri dish and it was covered with a glass lid.

The condition of the test insects was continuously observed. The time which was necessary for 100% destruction was determined.

The test insects the active compounds, the concentrations of the active compounds and the time at which there is 100% destruction can be seen from the following Table 7:

TABLE 7

(LT$_{100}$ test for Diptera/*Musca domestica*)

| Active compound | Active compound concentration of the solution in % by weight | LT$_{100}$ |
|---|---|---|
| (C$_2$H$_5$O)$_2$—P(=S)—O—C(CH$_3$)=CH—N=N—H (known) (B) | 0.2<br>0.02 | 105'<br>6 hrs = 75% |
| (CH$_3$O)$_2$—P(=S)—O—C(CH$_3$)=CH—N=N—H (known) (A) | 0.2 | 8 hrs = 70% |
| (C$_2$H$_5$O)$_2$—P(=S)—O—C(OC$_2$H$_5$)=N—N(CH$_3$)—N= (3) | 0.2<br>0.02<br>0.002 | 35'<br>75'<br>6 hrs = 90% |
| (C$_2$H$_5$O)$_2$—P(=S)—O—C(SCH$_3$)=N—N(C$_3$H$_7$-i)—N= (13) | 0.2<br>0.02<br>0.002 | 50'<br>210'<br>6 hrs = 40% |
| (C$_2$H$_5$O)$_2$—P(=S)—O—C(SCH$_3$)=N—N(CH$_3$)—N= (2) | 0.2<br>0.02 | 75'<br>6 hrs = 80% |
| (CH$_3$O)$_2$—P(=S)—O—C(SCH$_3$)=N—N(CH$_3$)—N= (1) | 0.2<br>0.02<br>0.002 | 65'<br>110'<br>6 hrs = 60% |
| (C$_2$H$_5$O)$_2$—P(=S)—O—C(OCH$_3$)=N—N(CH$_3$)—N= (12) | 0.2<br>0.02<br>0.002 | 35'<br>70'<br>6 hrs = 50% |
| C$_6$H$_5$—P(=S)(C$_2$H$_5$O)—O—C(OCH$_3$)=N—N(CH$_3$)—N= (11) | 0.2<br>0.02<br>0.002 | 95'<br>110'<br>6 hrs = 90% |

The active compound investigated, the concentration examined (mg/l), the parasites tested and the results obtained can be seen from Table 8 which follows:

TABLE 8

**(Tick test/*Boophilus microplus*)**

| Active compound | Active compound concentration in ppm | Inhibition of laying of eggs in % (*Boophilus microplus*/Biarra strain) |
|---|---|---|
| 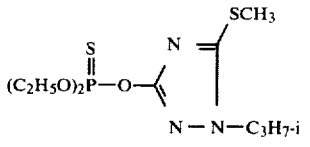 (13) | 10,000<br>1,000<br>100 | 100<br>100<br>>50 |
| 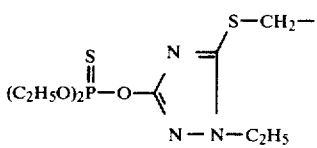 (10) | 10,000<br>1,000<br>100 | 100<br>100<br>100 |
| 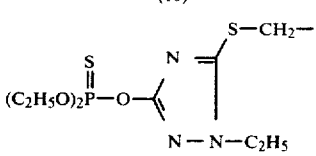 (9) | 10,000<br>1,000<br>100 | 100<br>100<br>100 |
| 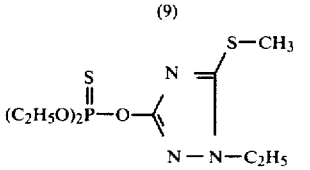 (7) | 10,000<br>1,000<br>100 | 100<br>100<br>100 |

EXAMPLE 8

Tick test

Solvent: 35 parts by weight of ethylene glycol monomethyl ether

Emulsifier: 35 parts by weight of nonylphenyl polyglycol ether

To prepare a suitable formulation, 3 parts by weight of active compound were mixed with 7 parts of the above-mentioned solvent-emulsifier mixture and the emulsion concentrate thus obtained was diluted with water to the particular desired concentration.

Adult, fully gorged female ticks of the species *Boophilus microplus* (sensitive or resistant) were dipped into these active compounds for one minute. After dipping groups of 10 female specimens of the different varieties of tick, the specimens were transferred into Petri dishes of which the bottom was covered with a filter disc of appropriate size.

After 10 days, the activity of the preparation of active compound was determined by determining the inhibition of laying of eggs, as compared to untreated control ticks. The effect is expressed in percent, with 100% meaning that no further eggs were laid and 0% indicating that the ticks laid eggs in normal amount.

EXAMPLE 9

Test with parasitic fly larvae

Solvent: 35 parts by weight of ethylene glycol monomethyl ether

Emulsifier: 35 parts by weight of nonylphenol polyglycol ether

To produce a suitable preparation of active compound, 30 parts by weight of the active substance in question were mixed with the stated amount of solvent which contained the above-mentioned proportion of emulsifier and the concentrate thus obtained was diluted with water to the desired concentration.

About 20 fly larvae (*Lucilia cuprina*) were introduced into a test tube which contained approximately 2 cm³ of horse muscle. 0.5 ml of the active compound preparation was applied to this horsemeat. After 24 hours the degree of destruction in percent was determined. 100% means that all the larvae were killed and 0% means that no larvae were killed.

The results obtained can be seen from Table 9 which follows:

TABLE 9

(Test with parasitic fly larvae/*Lucilia cuprina*)

| Active compound | Active compound concentration in ppm (w/v) | Degree of destruction in % (*Lucilia cuprina*/resistant) |
|---|---|---|
| 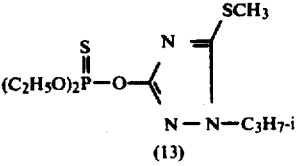 (13) | 100<br>30<br>10<br>3<br>1<br>0.3 | 100<br>100<br>100<br>100<br>100<br>0 |
| 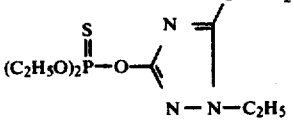 (9) | 100<br>10<br>1 | 100<br>100<br><50 |
| 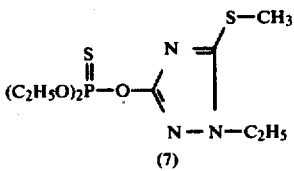 (7) | 100<br>10<br>1 | 100<br>100<br>100 |

EXAMPLE 10

Critical concentration test
Test nematode: *Meloidogyne incognita*
Solvent: 3 parts by weight of acetone
Emulsifier: 1 part by weight of alkylaryl polyglycol ether To produce a suitable preparation of active compound, 1 part by weight of active compound was mixed with the stated amount of solvent, the stated amount of emulsifier was added and the concentrate was diluted with water to the desired concentration.

The preparation of active compound was intimately mixed with soil which was heavily infested with the test namatodes. The concentration of the active compound in the preparation was of practically no importance; only the amount of active compound per unit volume of soil, which is given in ppm(w/v), was decisive. The soil was filled into pots, lettuce was sown in and the pots were kept at a greenhouse temperature of 27° C. After 4 weeks, the lettuce roots were examined for infestation with nematodes, and the degree of effectiveness of the active compound was determined as a percentage. The degree of effectiveness is 100% when infestation was completely avoided; it is 0% when the infestation was exactly the same as in the case of the control plants in untreated soil which had been infested in the same manner.

The active compound, the amounts applied and the results can be seen from the following Table 10:

TABLE 10

(*Meloidogyne incognita* test)

| Active compound | Degree of destruction in % at an active compound concentration of | | | | | | |
|---|---|---|---|---|---|---|---|
| | 20 | 10 | 5 | 2.5 | 1.25 | 0.625 | ppm |
| 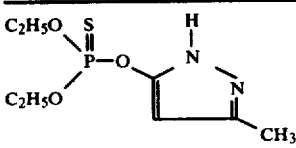 (known) (B) | 0 | | | | | | |
| 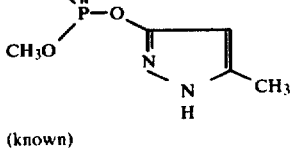 (known) (A) | 0 | | | | | | |

TABLE 10-continued
(Meloidogyne incognita test)

| Active compound | Degree of destruction in % at an active compound concentration of | | | | | | |
|---|---|---|---|---|---|---|---|
| | 20 | 10 | 5 | 2.5 | 1.25 | 0.625 | ppm |
| Compound (13): (C$_2$H$_5$O)$_2$P(S)—O—C(=N—N—C$_3$H$_7$-i)—SCH$_3$ (triazole) | 100 | 100 | 100 | 100 | 100 | 98 | |
| Compound (2): (C$_2$H$_5$O)$_2$P(S)—O—C(=N—N—CH$_3$)—SCH$_3$ | 100 | 100 | 100 | 99 | 98 | | |
| Compound (5): (iC$_3$H$_7$—NH)(C$_2$H$_5$O)P(S)—O—C(=N—N—C$_3$H$_7$i)—SCH$_3$ | 100 | 75 | | | | | |
| Compound (10): (C$_2$H$_5$O)$_2$P(S)—O—C(=N—N—C$_2$H$_5$)—SCH$_2$—CN | 100 | 97 | 50 | | | | |
| Compound (9): (C$_2$H$_5$O)$_2$P(S)—O—C(=N—N—C$_2$H$_5$)—SCH$_2$—CH=CH$_2$ | 100 | 100 | 98 | 97 | 50 | | |
| Compound (7): (C$_2$H$_5$O)$_2$P(S)—O—C(=N—N—C$_2$H$_5$)—S—CH$_3$ | 100 | 100 | 100 | 100 | 100 | 98 | |

The triazolyl derivatives (II) used as starting substances were prepared as exemplified below.

EXAMPLE 1

35.4 g (0.2 mole) of

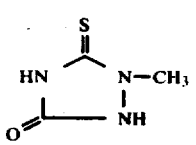

(prepared from

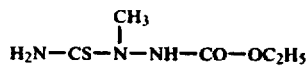

methylthiosemicarbazide and pyrocarbonic acid diethyl ester, melting point 170° C.) and 0.2 mole of sodium methylate—dissolved in 100 ml of methanol—were heated for 5 hours under reflux and subsequently evaporated under reduced pressure and the residue was dissolved in water and again precipitated with hydrochloric acid. 17 g (65% of theory) of the compound of the above formula, of melting point 250° C., were obtained. (VIIb)

Analogously, the following compounds were obtained from

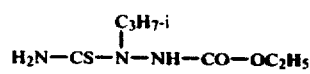

(prepared from N-iso-propylcarbonic acid ethyl ester hydrazide and potassium thiocyanate, melting point 168° C.) or from

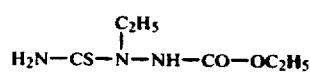

(obtained from N-ethylcarbonic acid ethyl ester hydrazide and potassium thiocyanate, melting point 133° C.), respectively:

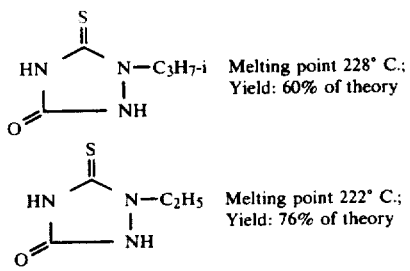 (VIIIc) Melting point 228° C.; Yield: 60% of theory

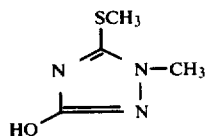 (VIIId) Melting point 222° C.; Yield: 76% of theory

EXAMPLE 2

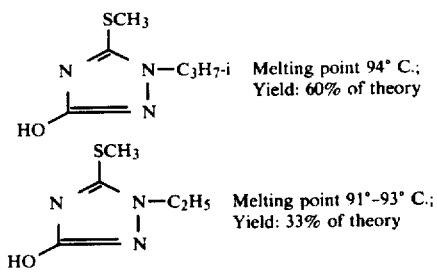 (IIIc)

13.1 g (0.1 mole) of the compound obtained in Example 1 and 6 g of potassium hydroxide were dissolved in 50 ml of water and 12.6 g of dimethyl sulfate were added. The batch was stirred for 2 hours at 25° C. and the reaction solution was extracted with methylene chloride and worked up in the usual manner. 14.3 g (98% of theory) of 1-methyl-3-hydroxy-5-methylmercapto-1,2,4-triazole of melting point 130° C. were obtained.

The following were prepared analogously:

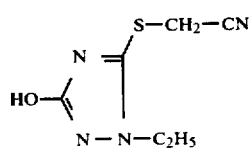 (IIId) Melting point 94° C.; Yield: 60% of theory (IIIe) Melting point 91°-93° C.; Yield: 33% of theory

EXAMPLE 3

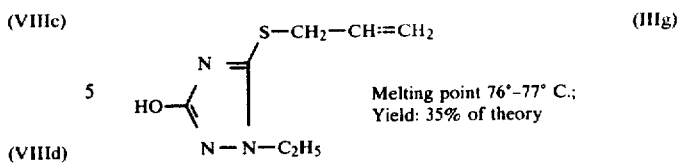 (IIIf)

0.5 mole of sodium methylate, followed by 38 g of chloroacetonitrile, were added to a solution of 73 g (0.5 mole) of 1-ethyl-3-hydroxy-triazole-5-thione in 300 ml of methanol, the temperature of the reaction mixture being 30° to 40° C. After stirring for 24 hours the precipitate which had separated out was filtered off, the filtrate was concentrated under reduced pressure and the residue was triturated with water, filtered off and dried. After recrystallization from acetonitrile, 19 g (20.6% of theory) of 1-ethyl-3-hydroxy-5-cyanomethylmercapto-1,2,4-triazole of melting point 127° C. were obtained.

The following compound was obtained analogously by reaction with allyl bromide:

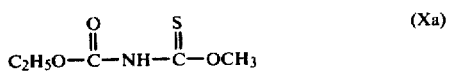 (IIIg) Melting point 76°-77° C.; Yield: 35% of theory

EXAMPLE 4

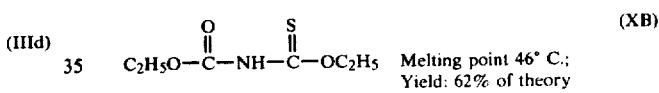 (Xa)

327 g of chloroformic acid ethyl ester were added to a solution or suspension of 300 g (3 moles) of potassium thiocyanate in 800 ml of dry acetone, during which addition the temperature of the mixture rose to 30°-40° C.; the mixture was stirred for 3 hours and 200 ml of methanol were then added at 50° to 60° C. After further stirring overnight, the solid constituents were filtered off, the filtrate was evaporated under reduced pressure and the residue was stirred up with water. After filtration and drying, 314 g (64% of theory) of N-carboethoxy-thiomethyl-urethane of melting point 48° C. were obtained.

The following compound was obtained analogously by reaction with chloroformic acid ethyl ester:

$C_2H_5O-\overset{O}{\underset{\|}{C}}-NH-\overset{S}{\underset{\|}{C}}-OC_2H_5$ (XB) Melting point 46° C.; Yield: 62% of theory

EXAMPLE 5

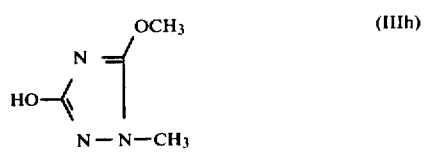 (IIIh)

46 g of methylhydrazine were added to 163 g (1 mole) of N-carboethoxy-thiomethylurethane—dissolved in 500 ml of methanol—during which addition the temperature of the reaction solution rose to 20°-30° C. The batch was then slowly warmed to 80° C. and was then boiled for 2 hours under reflux. After cooling the mixture, the residue was filtered off and recrystallized from methanol, whereupon 44 g (34% of theory) of 1-methyl-3-hydroxy-5-methoxy-1,2,4-triazole of melting point 216° C. were obtained.

The following compound was obtained analogously from N-carboethoxy-thioethylurethane:

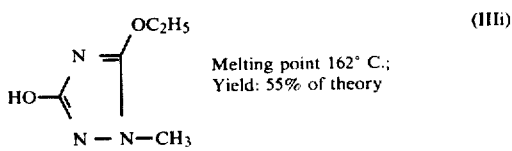 (IIIi) Melting point 162° C.; Yield: 55% of theory

EXAMPLE 6

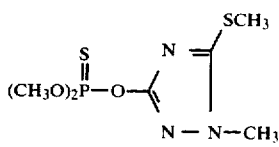

16 g (0.1 mole) of O,O-dimethylthionophosphoric acid diester chloride were added dropwise to a mixture of 159 g (0.1 mole) of 1-methyl-3-hydroxy-5-methylmercapto-1,2,4-triazole and 15 g of potassium carbonate in 250 ml of acetonitrile, during which addition the internal temperature slowly rose from 22° to 30° C. After stirring for four hours at room temperature and subsequently heating to 55°–60° C. for two hours, the reaction mixture was cooled and poured into water, and the batch was taken up in benzene. The organic phase was washed and dried, the solvent was evaporated under reduced pressure and the residue was subjected to "slight distillation". 19 g (71% of theory) of O,O-dimethyl-O-[1-methyl-5-methylmercapto-1,2,4-triazolyl-(3)]-thionophosphoric acid ester of refractive index $n_D^{25}$: 1.5311 were obtained.

The following compounds were prepared analogously:

TABLE 11

| | Compound | Physical properties (refractive index) | Yield (% of theory) |
|---|---|---|---|
| (2) | (C₂H₅O)₂P(S)—O—[SCH₃ / N=... / N—N—CH₃] | $n_D^{25}$: 1.5189 | 77 |
| (3) | (C₂H₅O)₂P(S)—O—[OC₂H₅ / N=... / N—N—CH₃] | $n_D^{23}$: 1.4892 | 88 |
| (4) | (CH₃O)₂P(S)—O—[SCH₃H / N=... / N—N—C₃H₇-i] | $n_D^{28}$: 1.5119 | 64 |
| (5) | i-C₃H₇—NH,C₂H₅O—P(S)—O—[SCH₃ / N=... / N—N—C₃H₇-i] | $n_D^{28}$: 1.5159 | 74 |
| (6) | C₆H₅,C₂H₅O—P(S)—O—[SCH₃ / N=... / N—N—C₃H₇-i] | $n_D^{28}$: 1.5612 | 76 |
| (7) | (C₂H₅O)₂P(S)—O—[SCH₃ / N=... / N—N—C₂H₅] | $n_D^{24}$: 1.5125 | 80 |
| (8) | (CH₃O)₂P(S)—O—[SCH₃ / N=... / N—N—C₂H₅] | $n_D^{24}$: 1.5224 | 71 |
| (9) | (C₂H₅O)₂P(S)—O—[S—CH₂—CH=CH₂ / N=... / N—N—C₂H₅] | $n_D^{24}$: 1.5160 | 86 |
| (10) | (C₂H₅O)₂P(S)—O—[S—CH₂—CN / N=... / N—N—C₂H₅] | $n_D^{24}$: 1.5184 | 71 |

TABLE 11-continued

| Compound | Physical properties (refractive index) | Yield (% of theory) |
|---|---|---|
| (11) Phenyl-P(=S)(OC₂H₅)-O-C(=N-OCH₃)-N(-)-N-CH₃ (cyclic) | $n_D^{28}$: 1.5576 | 58 |
| (12) (C₂H₅O)₂P(=S)-O-C(=N-OCH₃)-N(-)-N-CH₃ (cyclic) | $n_D^{24}$: 1.4887 | 75 |
| (13) (C₂H₅O)₂P(=S)-O-C(=N-SCH₃)-N(-)-N-C₃H₇-i (cyclic) | $n_D^{22}$: 1.5089 | 74 |
| (14) C₂H₅O-P(=S)(C₂H₅)-O-C(=N-SCH₃)-N(-)-N-C₂H₅ (cyclic) | $n_D^{21}$: 1.5278 | 68 |
| (15) n-C₃H₇O-P(=S)(OC₂H₅)-O-C(=N-SCH₃)-N(-)-N-C₃H₇-i (cyclic) | $n_D^{24}$: 1.5048 | 71 |
| (16) n-C₃H₇O-P(=S)(OCH₃)-O-C(=N-SCH₃)-N(-)-N-C₃H₇-i (cyclic) | $n_D^{24}$: 1.5090 | 68 |

The compounds in the following Table 12 were prepared by a process analogous to that of Example 6. In the table, the compounds are identified by the meanings of the symbols R, R', R" and R'" in formula (I), X being sulfur.

TABLE 12

| Cpd. No. | R | R' | R" | R'" |
|---|---|---|---|---|
| 17 | CH₃ | CH₃O | CH₂—CH=CH₂ | CH₃ |
| 18 | C₂H₅ | C₂H₅O | CH₂—CH=CH₂ | CH₃ |
| 19 | CH₃ | CH₃O | CH₂—CH=CH₂ | CH(CH₃)₂ |
| 20 | C₂H₅ | C₂H₅O | CH₂—CH=CH₂ | CH(CH₃)₂ |
| 21 | CH₃ | C₂H₅ | CH₂—CH=CH₂ | CH₃ |
| 22 | C₂H₅ | C₂H₅ | CH₂—CH=CH₂ | C₂H₅ |
| 23 | C₂H₅ | C₂H₅ | CH₂—CH=CH₂ | CH(CH₃)₂ |
| 24 | C₂H₅ | C₂H₅O | CH₂—CH=CH₂ | CH₂—CH₂—CN |
| 25 | C₂H₅ | C₂H₅O | CH₂—CH=CH—CH₃ | CH₃ |
| 26 | C₂H₅ | C₂H₅ | CH₂—CH=CH₂ | CH₂—CH₂—CN |
| 27 | CH₃ | CH₃O | CH₂—CH=CH—CH₃ | CH(CH₃)₂ |
| 28 | CH₃ | CH₃O | CH₂—CN | CH₃ |
| 29 | C₂H₅ | C₂H₅O | CH₂—CN | CH(CH₃)₂ |
| 30 | C₂H₅ | C₂H₅ | CH₂—CN | C₂H₅ |
| 31 | CH₃ | CH₃O | CH₂—CH₂—CN | CH₃ |
| 32 | C₂H₅ | C₂H₅O | CH₂—CH₂—CN | CH(CH₃)₂ |
| 33 | CH₃ | CH₃O | CH₃ | CH₂—CH₂—CN |
| 34 | C₂H₅ | C₂H₅ | CH₃ | CH₂—CH₂—CN |
| 35 | CH₃ | CH₃O | C₂H₅ | CH₂—CH₂—CN |
| 36 | C₂H₅ | C₂H₅O | C₂H₅ | CH₂—CH₂—CN |
| 37 | C₂H₅ | CH₃ | CH₃ | CH₂—CH₂—CN |
| 38 | CH₃ | CH₃ | CH₃ | CH₂—CH₂—CN |
| 39 | CH₃ | CH₃NH | CH₃ | CH₃ |
| 40 | CH₃ | C₂H₅NH | CH₃ | CH(CH₃)₃ |
| 41 | C₂H₅ | (CH₃)₂N | CH₃ | CH₂—CH₂—CN |
| 42 | C₂H₅ | (CH₃)₂CH—NH | CH₂—CH=CH₂ | CH₃ |
| 43 | C₂H₅ | (CH₃)₂CH—NH | CH₂—CH=CH₂ | CH(CH₃)₂ |
| 44 | C₂H₅ | (CH₃)₂CH—NH | CH₂CN | CH(CH₃)₂ |
| 45 | C₂H₅ | (CH₃)₂CH—NH | CH₂—CH=CH₂ | CH₂—CH₂—CN |
| 46 | C₂H₅ | C₂H₅O | CH₃ | CH(CN)CH₃ |

TABLE 12-continued

| Cpd. No. | R | R' | R" | R''' |
|---|---|---|---|---|
| 47 | C₂H₅ | C₂H₅O | CH₂—CH=CH₂ | CH(CN)CH₃ |

It will be appreciated that the instant specification and examples are set foth by way of illustration and not limitation, and that various modifications and changes may be made without departing from the spirit and scope of the present invention.

What is claimed is:

1. An 0-triazolylthionophosphoric acid ester of the formula

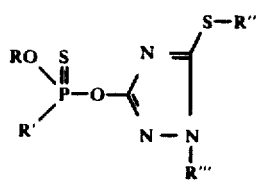

in which
R is alkyl of 1 to 6 carbon atoms,
R' is alkoxy of 1 to 6 carbon atoms,
R" is a cyanoalkyl of 1 to 4 carbon atoms, and
R''' is alkyl of 1 to 6 carbon atoms.

2. A compound according to claim 1, wherein such compound is O,O-diethyl-O-(1-isopropyl-5-cyanoethyl-mercapto-1,2,4-triazolyl-3)-thionophosphoric acid ester of the formula

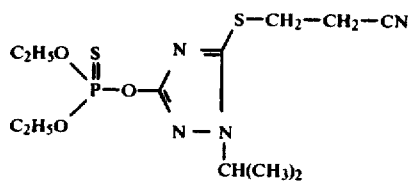

3. An insecticidal or acaricidal composition containing an insecticidally or acaricidally effective amount of a compound according to claim 1 in admixture with a diluent.

4. A method of combating insect or acarid pests which comprises applying to the pests or a habitat thereof an insecticidally or acaricidally effective amount of a compound according to claim 1.

5. The method according to claim 4 in which said compound is O,O-diethyl-O-(1-isopropyl-5-cyanoethyl-mercapto-1,2,4-triazolyl-3)-thionophosphoric acid ester.

* * * * *